US010695083B2

(12) United States Patent
Kase (10) Patent No.: US 10,695,083 B2
(45) Date of Patent: Jun. 30, 2020

(54) GRASPING TREATMENT INSTRUMENT

(71) Applicant: OLYMPUS CORPORATION, Hachioji-shi, Tokyo (JP)

(72) Inventor: Seigo Kase, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 228 days.

(21) Appl. No.: 15/832,108

(22) Filed: Dec. 5, 2017

(65) Prior Publication Data

US 2019/0159801 A1 May 30, 2019
US 2019/0274715 A9 Sep. 12, 2019

Related U.S. Application Data

(63) Continuation of application No. PCT/JP2016/076163, filed on Sep. 6, 2016.

(30) Foreign Application Priority Data

Sep. 17, 2015 (JP) .................... 2015-184121

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 18/1445* (2013.01);
(Continued)

(58) Field of Classification Search
CPC ....... A61B 2017/320072; A61B 2017/320093; A61B 2017/320094; A61B 2017/320095;
(Continued)

(56) References Cited

U.S. PATENT DOCUMENTS 6,129,735 A 10/2000 Okada et al.
2002/0188294 A1* 12/2002 Couture ............. A61B 18/1445
606/51

(Continued)

FOREIGN PATENT DOCUMENTS

JP 2011-200586 A 10/2011
JP 2014-121618 A 7/2014
(Continued)

OTHER PUBLICATIONS

Nov. 22, 2016 International Search Report issued in International Patent Application No. PCT/JP2016/076163.
(Continued)

*Primary Examiner* — Christopher A Flory
(74) *Attorney, Agent, or Firm* — Oliff PLC (57) ABSTRACT

A grasping treatment instrument includes a grasping piece, and a supporting member opening and closing relative to the grasping piece. A clamp member is provided between the supporting member and the grasping piece in open and close directions of the supporting member, and the clamp member includes an opposed surface opposed to the grasping piece, and a back surface facing to an opposite side of the opposed surface. The grasping treatment instrument includes a cover member made of a material having lower thermal conductivity than the clamp member, and the cover member covers the clamp member from the back surface side in a part on a distal side with respect to a position where the clamp member is pivotally supported.

12 Claims, 8 Drawing Sheets

(51) Int. Cl.
 *A61B 90/00* (2016.01)
 *A61B 17/28* (2006.01)
 *A61B 17/29* (2006.01)
 *A61B 18/08* (2006.01)

(52) U.S. Cl.
 CPC .............. *A61B 90/03* (2016.02); *A61B 17/29* (2013.01); *A61B 18/085* (2013.01); *A61B 2017/2825* (2013.01); *A61B 2017/2829* (2013.01); *A61B 2017/320072* (2013.01); *A61B 2090/08021* (2016.02)

(58) Field of Classification Search
 CPC ........... A61B 2017/320097; A61B 17/320092; A61B 90/03; A61B 18/1442
 See application file for complete search history.

(56) References Cited

U.S. PATENT DOCUMENTS

| | | | | |
|---|---|---|---|---|
| 2004/0122423 | A1* | 6/2004 | Dycus | A61B 90/03 606/51 |
| 2006/0189980 | A1* | 8/2006 | Johnson | A61B 18/1445 606/51 |
| 2008/0015567 | A1* | 1/2008 | Kimura | A61B 18/1442 606/41 |
| 2010/0331873 | A1* | 12/2010 | Dannaher | A61B 17/320092 606/169 |
| 2011/0004127 | A1* | 1/2011 | Okada | A61B 17/320092 601/2 |
| 2013/0046306 | A1* | 2/2013 | Evans | A61B 18/1445 606/51 |
| 2013/0303949 | A1 | 11/2013 | Kawaguchi et al. | |
| 2013/0345732 | A1* | 12/2013 | Dannaher | A61B 17/320092 606/169 |
| 2015/0018825 | A1* | 1/2015 | Takashino | A61B 18/085 606/52 |
| 2015/0148832 | A1 | 5/2015 | Boudreaux et al. | |
| 2015/0297289 | A1 | 10/2015 | Hirai et al. | |
| 2015/0327918 | A1 | 11/2015 | Sobajima et al. | |

FOREIGN PATENT DOCUMENTS

| | | |
|---|---|---|
| JP | 5666068 B1 | 2/2015 |
| WO | 2014/148280 A1 | 9/2014 |
| WO | 2014/196641 A1 | 12/2014 |
| WO | 2015/081039 A1 | 6/2015 |

OTHER PUBLICATIONS

Dec. 21, 2018 extended Search Report issued in European Patent Application No. 16846321.4.
Mar. 20, 2018 International Preliminary Report on Patentability issued in International Patent Application No. PCT/JP2016/076163.
Feb. 3, 2020 Office Action issued in Chinese Patent Application No. 201680049962.3.

* cited by examiner

GRASPING TREATMENT INSTRUMENT

CROSS-REFERENCE TO RELATED APPLICATIONS

This is a Continuation Application of PCT Application No. PCT/JP2016/076163, filed Sep. 6, 2016 and based upon and claiming the benefit of priority from prior Japanese Patent Application No. 2015-184121, filed Sep. 17, 2015, the entire contents of which are incorporated herein by reference.

BACKGROUND OF THE INVENTION

1. Field of the Invention

The present invention relates to a grasping treatment instrument provided with an end effector in which a space between a pair of grasping pieces is openable and closable.

2. Description of the Related Art

U.S. Patent Application Publication No. 2013/0303949 discloses a grasping treatment instrument provided with an end effector in which a space between a pair of grasping pieces is openable and closable. In this grasping treatment instrument, a rod that transmits ultrasonic vibration has a part projecting from a sheath, and this projecting part forms a first grasping piece as one of the grasping pieces. A second grasping piece as the other grasping piece includes a supporting member that is attached in a manner to be rotatable with respect to the sheath, and a clamp member that is attached in a manner to be swingable with respect to the supporting member. The clamp member is provided with an opposed surface that is opposed to the first grasping piece. The grasping treatment instrument performs treatment using treatment energy with a treated target being grasped between the first grasping piece and the opposed surface of the clamp member.

BRIEF SUMMARY OF THE INVENTION

According to one aspect of the invention, a grasping treatment instrument including: a grasping piece; a supporting member which is configured to open and close with respect to the grasping piece; a clamp member which is pivotally supported by the supporting member, and which is provided between the supporting member and the grasping piece in open and close directions of the supporting member, the clamp member including an opposed surface which is opposed to the grasping piece, and a back surface which faces to an opposite side of the opposed surface; and a cover member which is made of a material having lower thermal conductivity than the clamp member, and which is attached to the clamp member from a back surface side, the cover member covering the clamp member from the back surface side in a part on a distal side with respect to a position where the clamp member is pivotally supported.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

The first embodiment of the present invention will be explained with reference to FIGS. 1 to 6.

Figure 1:
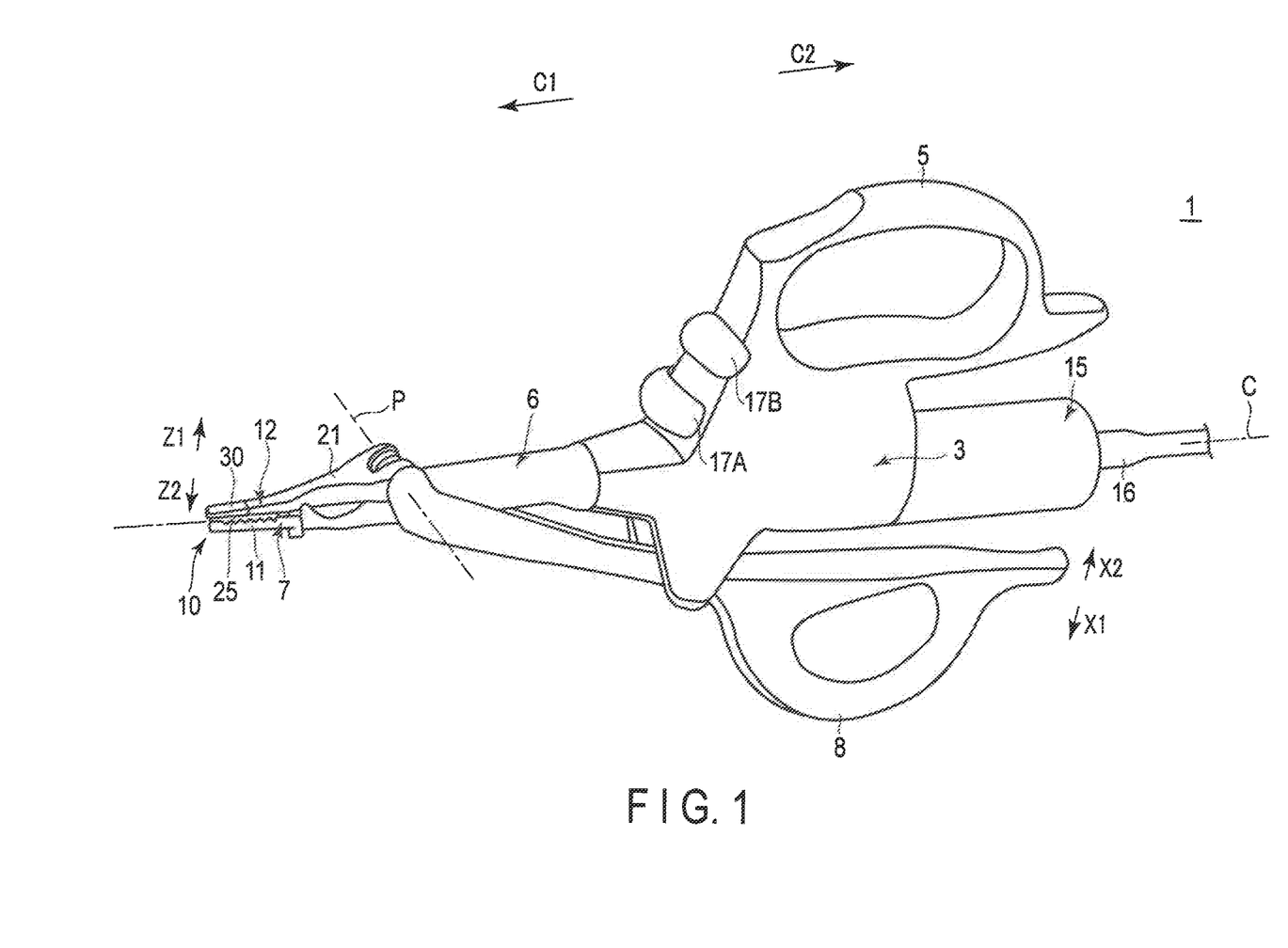
FIG. 1 is a perspective view schematically showing a grasping treatment instrument according to a first embodiment.

FIG. 1 is a view showing a grasping treatment instrument (a forceps-type treatment instrument) 1 according to the present embodiment. As shown in FIG. 1, the grasping treatment instrument 1 has a longitudinal axis C. Herein, the direction parallel to the longitudinal axis C is defined as a longitudinal axial direction. In the longitudinal axial direction, one side is defined as a distal side (the side indicated by the arrow C1 in FIG. 1) while the other side opposite to the distal side is defined as a proximal side (the side indicated by the arrow C2 in FIG. 1).

The grasping treatment instrument 1 includes a holdable housing 3. The housing 3 includes a grip (a stationary handle) 5. The grip 5 is positioned away from the longitudinal axis C toward one side in a direction intersecting with (substantially perpendicular to) the longitudinal axis C. A sheath 6 is fixed to the housing 3 from the distal side. The sheath 6 is extended along the longitudinal axis C (in a manner to be substantially coaxial with the longitudinal axis C) from the proximal side to the distal side. A rod 7 is extended from the inside of the housing 3 through the inside of the sheath 6 toward the distal side. The rod 7 is extended along the longitudinal axis C in a manner to be substantially coaxial with the longitudinal axis C. In the present embodiment, the rod 7 is made of a material having high vibration transmissibility and electrical conductivity. The distal portion of the rod 7 projects from the distal end of the sheath 6 toward the distal side. In the present embodiment, a part of the rod 7, which projects from the sheath 6, forms a first grasping piece (a grasping piece) 11.

A handle (movable handle) 8 and a second grasping piece 12 are rotatably attached to the distal portion of the sheath 6. The handle 8 and the second grasping piece 12 rotate together around a rotation axis P with respect to the housing 3, the sheath 6, and the rod 7. The rotation axis P passes through a position where the handle 8 and the second grasping piece 12 are attached to the sheath 6, and is extended in the direction intersecting with (substantially perpendicular to) the longitudinal axis C. The handle 8 is extended from the rotation axis P toward the proximal side. The second grasping piece 12 is extended from the rotation axis P toward the distal side. The handle 8 is positioned on the opposite side of the grip 5 with the longitudinal axis C as a center. The second grasping piece 12 is positioned on the same side as the grip 5 with the longitudinal axis C as the center.

By rotation around the rotation axis P, the handle 8 performs an opening action (the arrow X1 in FIG. 1) with respect to the housing 3. By this action, the second grasping piece 12 performs an opening action (the arrow Z1 in FIG. 1) with respect to the first grasping piece 11. By rotation around the rotation axis P, furthermore, the handle 8 performs a closing action (the arrow X2 in FIG. 1) with respect to the housing 3. By this action, the second grasping piece 12 performs a closing action (the arrow Z2 in FIG. 1) with respect to the first grasping piece 11. That is, the second grasping piece 12 is openable and closable with respect to the first grasping piece 11. In a state where the second grasping piece 12 is opening or closing with respect to the first grasping piece 11, the handle 8 rotates together with the second grasping piece 12 with respect to the first grasping piece 11 and the sheath 6. In the present embodiment, the pair of grasping pieces 11 and 12 form an end effector 10 that treats a treated target such as living tissue. The space between the pair of grasping pieces 11 and 12 is opened or closed by an opening action or a closing action of the second grasping piece 12 with respect to the first grasping piece 11. By closing a space between the grasping pieces 11 and 12 with a treated target being arranged therebetween, this treated target is grasped by the end effector 10. In the present embodiment, the open and close directions (the directions indicated by the arrows X1 and X2 in FIG. 1) of the handle 8 and the open and close directions (the directions indicated by the arrows Z1 and Z2 in FIG. 1) of the second grasping piece 12 (the end effector 10) intersect with (are substantially perpendicular to) the longitudinal axis C and also intersect with (are substantially perpendicular to) the rotation axis P.

A transducer unit 15 is coupled to the housing 3 from the proximal side. The transducer unit 15 is provided with an ultrasonic transducer (not shown). Inside the housing 3, the ultrasonic transducer is coupled to the rod 7 from the proximal side. A cable 16 has one end connected to the transducer unit 15, and the other end connected to an energy control device (not shown). Operation buttons (energy operation input sections) 17A and 17B are attached to the housing 3. When operation input is performed using the operation button 17A, electric energy is supplied from the energy control device to the ultrasonic transducer. In this manner, ultrasonic vibration is generated in the ultrasonic transducer, and is transmitted to the first grasping piece 11 through the rod 7. By using this transmitted ultrasonic vibration, the end effector 10 performs treatment on a treated target being grasped. When operation input is performed using the operation button 17B, high-frequency electric energy is supplied from the energy control device to the first grasping piece 11 and the second grasping piece 12. A treated target, which is grasped, is treated by applying a high-frequent current thereto.

Figure 2:
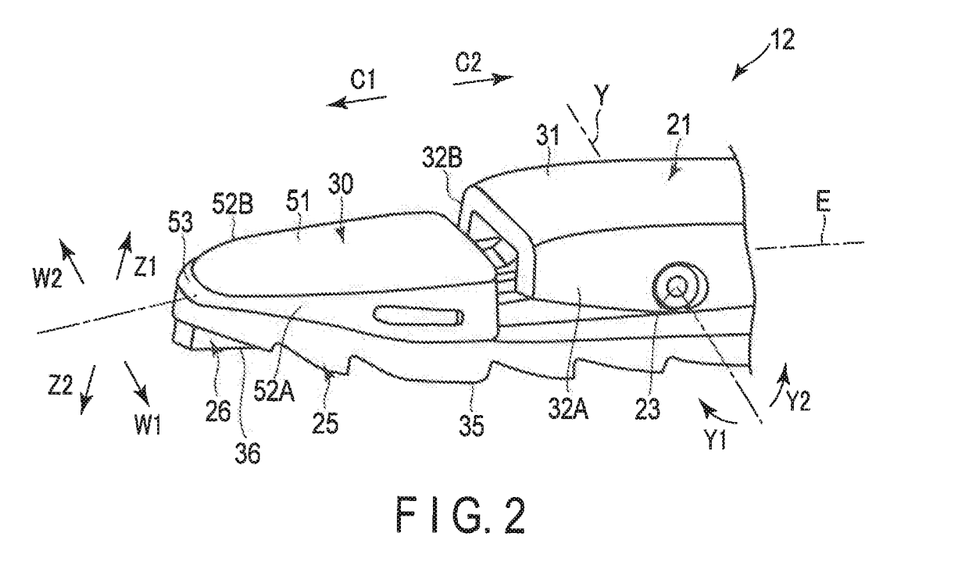
FIG. 2 is a perspective view schematically showing a second grasping piece according to the first embodiment.

FIG. 2 is a view showing a configuration of the second grasping piece 12. As shown in FIGS. 1 and 2, the second grasping piece 12 includes a supporting member 21 that is attached to the sheath 6 in a manner to be rotatable around the rotation axis P. The rotation axis P passes through the supporting member 21. The handle 8 is fixed to the supporting member 21. The supporting member 21 and the handle 8 are integrally formed. This enhances heat transference from the supporting member 21 to the handle 8. The handle 8 rotates together with the supporting member 21 around the rotation axis P with respect to the first grasping piece 11.

The second grasping piece 12 includes a clamp member (an electrode member) 25, a pad member 26, and a cover member 30. In the second grasping piece 12, as shown in FIG. 2, the clamp member 25 is attached to the supporting member 21 through a supporting pin 23. The clamp member 25 includes the proximal portion and the distal portion, and is extended along the extending axis E from the proximal portion to the distal portion. In a state where a space between the pair of grasping pieces 11 and 12 is at maximum closure, the extending axis E of the clamp member 25 is substantially parallel to the longitudinal axis C. The clamp member 25 is positioned between the supporting member 21 and the first grasping piece 11 in the open and close directions (the directions indicated by the arrows Z1 and Z2 in FIG. 2) of the second grasping piece 12. The clamp member 25 is made of a material having electrical conductivity and high heat conductivity, such as a metal. The pad member 26 is fixed to the clamp member 25. The pad member 26 is extended in the direction along the extending axis E from the proximal portion to the distal portion of the clamp member 25. The pad member 26 is made of a material having electrical insulation, such as PTFE (polytetrafluoroethylene).

Figure 3:
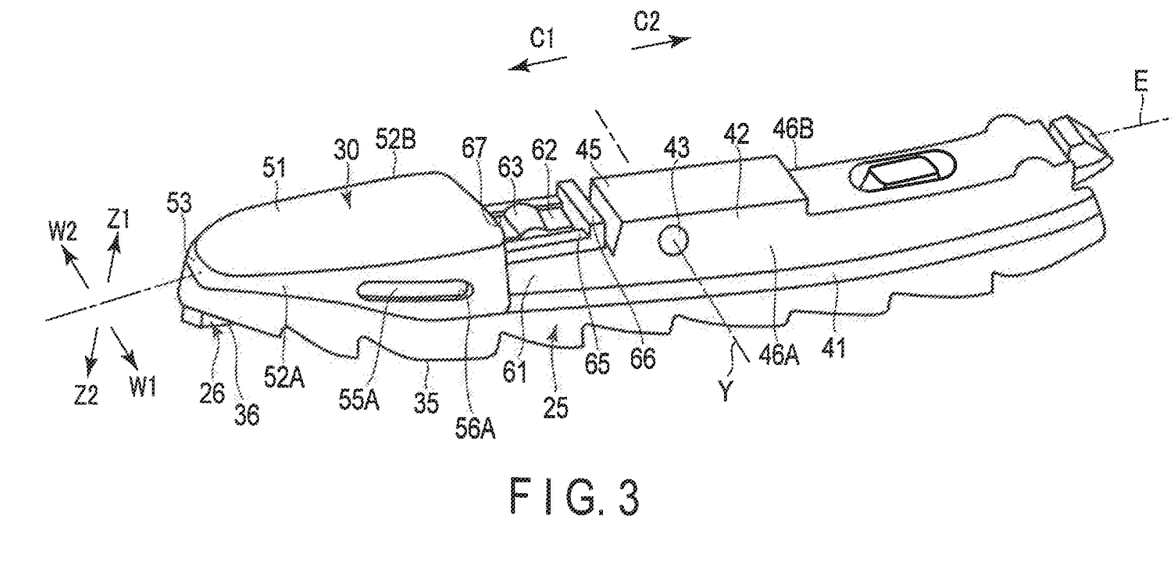
FIG. 3 is a perspective view schematically showing a clamp member, a pad member, and a cover member according to the first embodiment.
Figure 4:
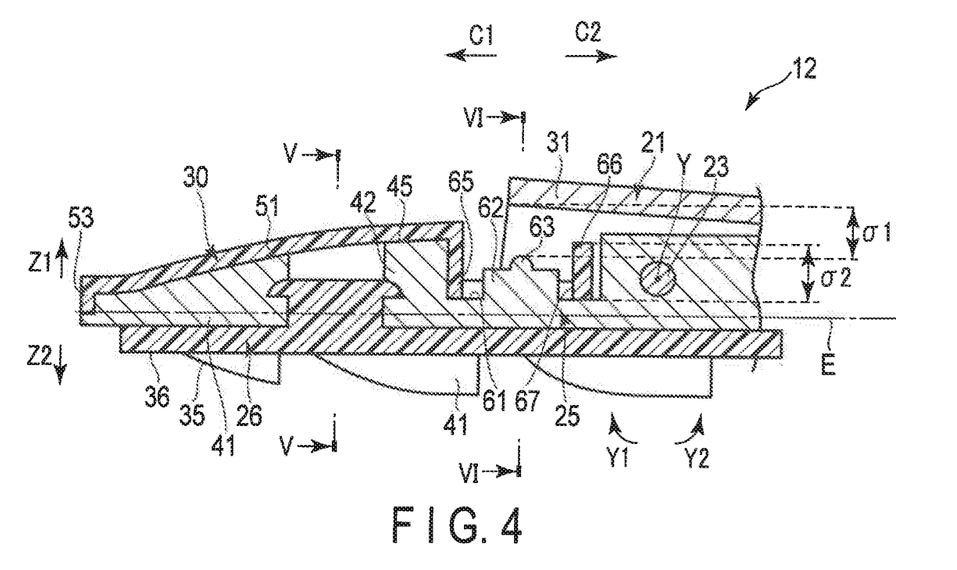
FIG. 4 is a cross-sectional view, taken in a cross section perpendicular to width directions, schematically showing a second grasping piece according to the first embodiment.
Figure 5:
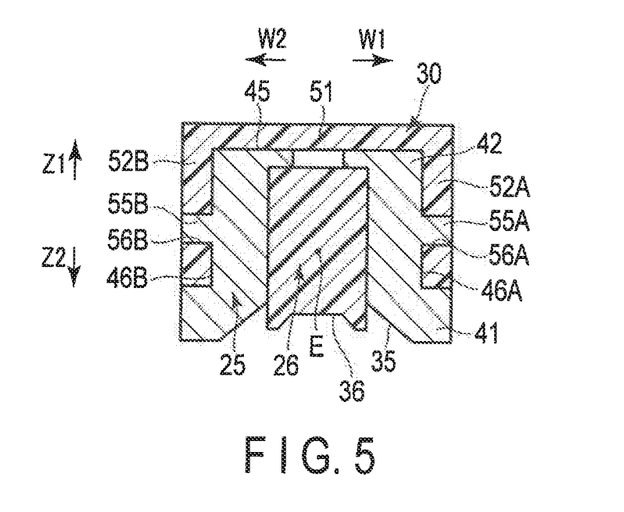
FIG. 5 is a cross-sectional view taken along line V-V in FIG. 4.
Figure 6:
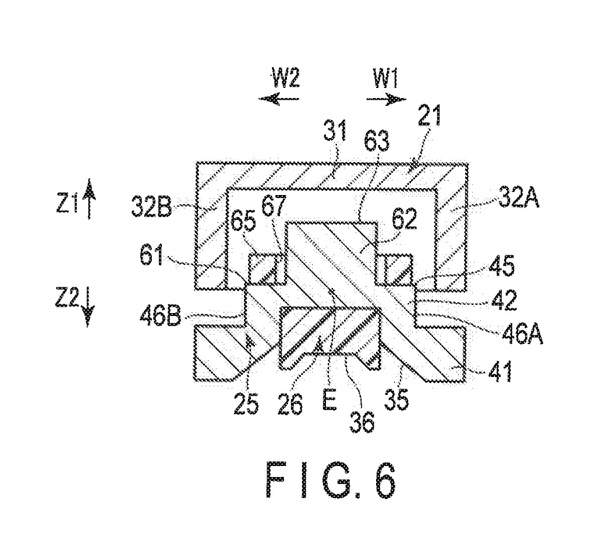
FIG. 6 is a cross-sectional view taken along line VI-VI in FIG. 4.

FIG. 3 is a view showing a configuration of the clamp member 25, the pad member 26, and the cover member 30. Width directions (the directions indicated by the arrows W1 and W2 in FIG. 2) of the second grasping piece 12 (the clamp member 25), which intersect with (are substantially perpendicular to) the extending directions (the extending axis E) of the clamp member 25 and also intersect with (are substantially perpendicular to) the open and close directions of the second grasping piece 12. FIG. 4 shows the second grasping piece 12, taken in a cross section perpendicular to the width directions. FIG. 5 shows a cross section taken along line V-V in FIG. 4. FIG. 6 is a cross section taken along line VI-VI in FIG. 4. FIGS. 5 and 6, therefore, show the cross sections that are substantially perpendicular to the extending directions (the extending axis E) of the clamp member 25.

As shown in FIGS. 2 to 6, the clamp member 25 includes a clamp opposed surface (an opposed surface) 35 that is opposed to the first grasping piece 11. The clamp opposed surface 35 faces to a side (the side indicated by the arrow Z2 in each of FIGS. 2 to 6) to which the second grasping piece 12 is moved in its closing action with respect to the first grasping piece 11. The pad member 26 includes an abutting surface 36 that is opposed to the first grasping piece 11 and can abut on the first grasping piece 11. In the present embodiment, the clamp opposed surface 35 and the abutting surface 36 form an opposed surface of the second grasping piece 12, which is opposed to the first grasping piece 11. The clamp opposed surface 35 and the abutting surface 36 are extended in a direction along the extending axis E (the longitudinal axis C) from the proximal portion to the distal portion of the clamp member 25 (that is, from the proximal portion to the distal portion of the second grasping piece 12). In a state where a space between the pair of grasping pieces 11 and 12 is at maximum closure, the abutting surface 36 of the pad member 26 abuts on the first grasping piece 11. Even in a state where the abutting surface 36 abuts on the first grasping piece 11, the clamp opposed surface 35 is positioned away from the first grasping piece 11 so that the clamp member 25 has no contact with the first grasping piece 11.

The clamp member 25 includes a clamp back surface (a back surface) 45 facing to the opposite side of the clamp opposed surface 35. The clamp back surface 45 faces to a side (the side indicated by the arrow Z1 in each of FIGS. 2 to 6) to which the second grasping piece 12 is moved in its opening action with respect to the first grasping piece 11. The clamp member 25 includes a first clamp side surface (the first side surface) 46A which faces to one side (the side indicated by the arrow W1 in each of FIGS. 2, 3, 5, and 6) in the width directions of the second grasping piece 12 (the clamp member 25), and a second clamp side surface (the second side surface) 46B which faces to the opposite side (the side indicated by the arrow W2 in each of FIGS. 2, 3, 5, and 6) of the first clamp side surface 46A. The clamp back surface 45 and the clamp side surfaces 46A and 46B are extended in the direction along the extending axis E (the longitudinal axis C) from the proximal portion to the distal portion of the clamp member 25 (that is, from the proximal portion to the distal portion of the second grasping piece 12).

The clamp member 25 includes a clamp base 41 that forms the clamp opposed surface 35, and a clamp projection 42 that projects from the clamp base 41 to a back surface side (the side indicated by the arrow Z1 in each of FIGS. 2 to 6). The clamp base 41 and the clamp projection 42 are extended in the direction along the extending axis E (longitudinal axis C) from the proximal portion to the distal portion of the clamp member 25 (that is, the proximal portion to the distal portion of the second grasping piece 12). In the present embodiment, a projection end surface of the clamp projection 42 forms the clamp back surface 45. In every position in the direction along the extending axis E, the dimension of the clamp projection 42 is smaller than the dimension of the clamp base 41 in terms of the dimension in the width directions of the second grasping piece 12. The clamp side surfaces 46A and 46B are extended between the clamp opposed surface 35 and the clamp back surface 45 in the open and close directions of the second grasping piece 12. In the present embodiment, the clamp base 41 and the clamp projection 42 form the clamp side surfaces 46A and 46B.

The supporting member 21 is attached to the clamp member 25 from the back surface side. The supporting member 21 covers the clamp projection 42 of the clamp member 25, from the back surface side and both sides in the width directions, in the proximal portion and the middle portion of the clamp member 25 (the portions other than the distal portion of the clamp member 25) in the direction along the extending axis E. The supporting member 21 includes: a member back wall 31 that covers the clamp projection 42 from the back surface side; a first member side wall 32A that covers the clamp projection 42 from one side in the width directions of the second grasping piece 12; and a second member side wall 32B that covers the clamp projection 42 from the opposite side of the first member side wall 32A. In the proximal portion and the middle portion of the clamp member 25 in the direction along the extending axis E, therefore, the member back wall 31 covers the clamp back surface 45 from the back surface side. In the proximal portion and the middle portion of the clamp member 25 in the direction along the extending axis E, therefore, the first member side wall 32A covers the first clamp side surface 46A from one side in the width directions of the second grasping piece 12 while the second member side wall 32B covers the second clamp side surface 46B from the opposite side of the first member side wall 32A. The member back wall 31 forms the back surface of the supporting member 21. In the present embodiment, the member back wall 31 also forms a part of the back surface of the second grasping piece 12.

In the clamp projection section 42 of the clamp member 25, a through-hole 43 which penetrates the clamp side walls 46A and 46B is formed. The through-hole 43 is extended in the width directions of the second grasping piece 12. The supporting pin 23 that couples the clamp member 25 with the supporting member 21 is inserted through the through-hole 43. One end of the supporting pin 23 is connected to the first member side wall 32A while the other end of the supporting pin 23 is connected to the second member side wall 32B. Accordingly, the clamp member 25 is pivotally supported by the supporting member 21, and is swingable around a swing axis Y with respect to the supporting member 21 in swing directions (the directions indicated by the arrows Y1 and Y2 in each of FIGS. 2 and 4). The swing axis Y is substantially coaxial with the center axis of the supporting pin 23. In the present embodiment, the swing axis Y is extended in the width directions of the second grasping piece 12. The swing axis Y of the clamp member 25 therefore intersects with (are substantially perpendicular to) the extending directions (the extending axis E) of the clamp member 25, while intersecting with (being substantially perpendicular to) the open and close directions of the second grasping piece 12. The swing axis Y passes through the middle portion of the clamp member 25 (the clamp projection 42), in the direction along the extending axis E. The distal end of the supporting member 21 is positioned on the distal side (the side indicated by the arrow C1 in each of FIGS. 2 to 4) with respect to the swing axis Y. The clamp member 25 is swingably attached to the supporting member 21. This makes it hard to increase heat transference from the clamp member 25 to the supporting member 21.

When the clamp member 25 swings to one side (the side indicated by the arrow Y1 in each of FIGS. 2 and 4) in the swing directions with respect to the supporting member 21, the clamp back surface 45 comes close to the supporting member 21 on the distal side with respect to the swing axis Y, whereas the clamp opposed surface 35 comes close to the first grasping piece 11 on the proximal side (the side indicated by the arrow C2 in each of FIGS. 2 to 4) with respect to the swing axis Y. On the distal side with respect to the swing axis Y, abutment of the clamp back surface 45 on the member back wall 31 of the supporting member 21 restricts the clamp member 25 from swinging to one side in the swing directions. Swinging of the clamp member 25 to the other side (the side indicated by the arrow Y2 in each of FIGS. 2 and 4) in the swing directions with respect to the supporting member 21, on the other hand, brings the clamp opposed surface 35 close to the first grasping piece 11 on the distal side with respect to the swing axis Y, while bringing the clamp back surface 45 close to the supporting member 21 on the proximal side with respect to the swing axis Y. On the proximal side with respect to the swing axis Y, abutment of the clamp back surface 45 on the member back wall 31 of the supporting member 21 restricts the clamp member 25 from swinging to the other side in the swing directions. The pad member 26 is fixed to the clamp member 25. Thus, when the clamp member 25 swings, the pad member 26 swings together with the clamp member 25 around the swing axis Y with respect to the supporting member 21. FIG. 4 shows a state where the clamp member 25 swings farthest to the side indicated by the arrow Y2. In the state shown by FIG. 4, the clamp back surface 45 is separated farthest from the member back wall 31 on the distal side with respect to the swing axis Y.

The cover member 30 is attached to the distal portion of the clamp member 25 from the back surface side. In the distal portion of the clamp member 25 in the direction along the extending axis E, the cover member 30 covers the clamp projection 42 of the clamp member 25 from the back surface side, both sides in the width directions, and the distal side. On the distal side with respect to the swing axis Y (that is, the position where the clamp member 25 is pivotally supported by the supporting member 21), in the present embodiment, the cover member 30 covers the clamp projection 42 of the clamp member 25, from the back surface, both sides in the width directions, and the distal side. The cover member 30 is made of an elastic material having electrical insulation, and heat conductivity lower than the clamp member 25. The cover member 30 is, furthermore, made of a material having appropriate heat resistance. The cover member 30 is made of resin such as PEEK (polyether ether ketone), PI (polyimide), PAI (polyamide-imide), etc.

The cover member 30 includes: a cover back wall (a back wall) 51 that covers the clamp projection 42 from the back surface side; a first cover side wall (a first side wall) 52A that covers the clamp projection 42 from one side in the width directions of the second grasping piece 12; a second cover side wall (a second side wall) 52B that covers the clamp projection 42 from the opposite side of the first cover side wall 52A; and a cover distal wall 53 that covers the clamp projection 42 from the distal side. In the distal portion (the distal side with respect to the swing axis Y) of the clamp member 25 in the direction along the extending axis E, the cover back wall 51 covers the clamp back surface 45 from the back surface side. In the distal portion of the clamp member 25 in the direction along the extending axis E, the first cover side wall 52A covers the first clamp side surface 46A from one side in the width directions of the second grasping piece 12, while the second cover side wall 52B covers the second clamp side surface 46B from the opposite side of the first cover side wall 52A. The cover back wall 51 forms the back surface of the cover member 30. In the present embodiment, the cover back wall 51 also forms a part of the back surface of the second grasping piece 12. In the distal portion of the second grasping piece 12, the cover back wall 51 of the cover member 30 thus forms the back surface. The cover distal wall 53 forms the distal surface of the cover member 30. In the present embodiment, the cover distal wall 53 also forms a part of the distal surface of the second grasping piece 12.

The proximal end of the cover back wall 51 and the proximal ends of the cover side walls 52A and 52B are positioned on the distal side with respect to the swing axis Y and the distal end of the supporting member 21. The cover member 30 covers the clamp projection 42 within a range from the proximal end of the cover back wall 51 and the proximal ends of the cover side walls 52A and 52B to the distal end of the cover member 30 in the direction along the extending axis E. In the direction along the extending axis E, therefore, a range in which the cover member 30 covers the clamp projection 42 is positioned on the distal side with respect to a range in which the supporting member 21 covers the clamp projection 42, with no overlap between these ranges.

The first clamp side surface 46A includes a first engaging convex section 55A that projects to the outside (the side away from the extending axis E) in the width directions of the second grasping piece 12. The second clamp side surface 46B includes a second engaging convex section 55B that projects to the outside (the side away from the extending axis E) in the width directions of the second grasping piece 12. The engaging convex sections 55A and 55B are provided in the clamp projection 42 and are formed in the distal portion of the clamp member 25. The engaging convex sections 55A and 55B are positioned on the distal side with respect to the swing axis Y and the distal end of the supporting member 21.

In the first cover side wall 52A, a first engaging hole 56A that penetrates the first cover side wall 52A in the width directions of the second grasping piece 12 is formed. In the second cover side wall 52B, a second engaging hole 56B that penetrates the second cover side wall 52B in the width directions of the second grasping piece 12 is formed. The engaging holes 56A and 56B are positioned on the distal side with respect to the proximal end of the cover back wall 51 and the proximal ends of the cover side walls 52A and 52B. FIG. 5 shows a cross section that passes through the engaging convex sections 55A and 55B and the engaging holes 56A and 56B.

By using elastic deformation of the cover member 30, the first engaging hole (the first cover-side engaging section) 56A engages with the first engaging convex section (the first clamp-side engaging section) 55A by snap fitting. Similarly, by using elastic deformation of the cover member 30, the second engaging hole (the second cover-side engaging section) 56B engages with the second engaging convex section (the second clamp-side engaging section) 55B by snap fitting. Each of the engaging holes 56A and 56B engages with its corresponding engaging convex section (55A or 55B) so that the cover member 30 is attached to the clamp member 25 from the back surface side. The cover member 30 to be attached to the clamp member 25 swings together with the clamp member 25 around the swing axis Y with respect to the supporting member 21.

In a state where the cover member 30 is attached to the clamp member 25, the cover member 30 comes in contact with the clamp back surface 45 of the clamp member 25, thereby being pressed against the back surface side, particularly in portions on the distal side with respect to the engaging holes 56A and 56B. Accordingly, pressing by the clamp member 25 elastically deforms the cover back wall 51 of the cover member 30 from a state where the cover member 30 is not attached to the clamp member 25. Due to elastic deformation of the cover back wall 51 of the cover member 30, an elastic force (a reactive force) acts on the cover member 30 toward the opposed surface side (the side indicated by the arrow Z2 in each of FIGS. 2 to 6), particularly in portions on the distal side with respect to the engaging holes 56A and 56B. Since an elastic force acts on the cover member 30 toward the opposed surface side, the cover member 30 is brought in close contact with the clamp member 25 (the clamp base 41 and the clamp projection 42) without any clearance, on the outer surface of the second grasping piece 12. Specifically, the cover back wall 51 of the cover member 30 is brought in close contact with the clamp back surface 45 of the clamp member 25.

The clamp back surface 45 of the clamp member 25 (the clamp projection 42) is provided with an installation surface 61 between the swing axis Y and the engaging convex sections 55A and 55B in the direction along the extending axis E. On the clamp back surface 45 of the clamp member 25, a locking projection 62 that projects to the back surface side with the installation surface 61 as a base surface is formed. On the clamp back surface 45 of the clamp member 25, a regulating projection 63 that projects further to the back surface side than the locking projection 62 is formed. The locking projection 62 and the regulating projection 63 are positioned between the swing axis Y and the engaging convex sections 55A and 55B in the direction along the extending axis E. The member back wall 31 of the supporting member 21 covers the regulating projection 63 from the back surface side. In a state where the regulating projection 63 is separated farthest from the member back wall 31 of the supporting member 21 (that is, a state where the clamp member 25 swings most to the side indicated by the arrow Y2), a projection end (an end on the back surface side) of the regulating projection 63 is separated from the member back wall 31 of the supporting member 21 by separation distance σ1 in the open and close directions of the second grasping piece 12 (see FIG. 4).

The cover member 30 includes an insertion piece 65 that projects to the proximal side with respect to the proximal end of the cover back wall 51 and the proximal ends of the cover side walls 52A and 52B. In the insertion piece 65 according to the present embodiment, a through-hole 67 that penetrates the insertion piece 65 in the open and close directions of the second grasping piece 12 is formed. The insertion piece 65 is formed in a ring shape. The insertion piece 65 includes a stopper projection 66 that projects further to the back surface side than the other portions of the insertion piece 65. The stopper projection 66 is positioned on the proximal side with respect to the through-hole 67 and forms the proximal end of the cover member 30. In the stopper projection 66, the insertion piece 65 has height dimension σ2 in the open and close directions of the second grasping piece 12 (the height direction of the stopper projection 66). That is, in the stopper projection 66, a distance from the edge (the root) on the opposed surface side to the edge (the projection edge) on the back surface side corresponds to the height dimension σ2 (see FIG. 4). The height dimension σ2 of the stopper projection 66 is smaller than the separation distance σ1 of the projection edge of the regulating projection 63 from the member back wall 31 of the supporting member 21 in a state where the regulating projection 63 is separated farthest away from the member back wall 31 of the supporting member 21.

The insertion piece 65 of the cover member 30 is inserted from the distal side, between the supporting member 21 and the clamp member 25 in the open and close directions of the second grasping piece 12 (the supporting member 21). The locking projection 62 and the regulating projection 63 of the clamp member 25 are inserted into the through-hole 67 of the insertion piece 65 so that the insertion piece 65 engages with the locking projection 62. Thus, the insertion piece 65 is installed on the installation surface 61 in the clamp back surface 45. In a state where the insertion piece 65 engages with the locking projection 62, the stopper projection 66 of the insertion piece 65 is positioned on the proximal side with respect to the locking projection 62, and is positioned on the distal side with respect to swing axis Y.

The height dimension σ2 of the stopper projection 66 is smaller than the separation distance σ1 of the projection edge of the regulating projection 63 from the member back wall 31 of the supporting member 21. Thus, the regulating projection 63 regulates the stopper projection 66 from moving to the distal side, even in a state where the regulating projection 63 is separated farthest away from the member back wall 31 of the supporting member 21. That is, the regulating projection 63 regulates movement of the stopper projection 66 to the distal side, regardless of a position of the clamp member 25 with respect to the supporting member 21, which changes depending on swinging around the swing axis Y. Accordingly, removal of the insertion piece 65 from a space between the supporting member 21 and the clamp member 25 is prevented no matter where the clamp member 25 is positioned with respect to the supporting member 21. In the present embodiment, the regulating projection 63 of the clamp member 25 and the member back wall 31 of the supporting member 21 regulate movement of the insertion piece 65 in a manner wherein the insertion piece 65 is prevented from being removed from the space between the supporting member 21 and the clamp member 25. The regulating projection 63 and the member back wall 31 form a regulating section that regulates movement of the insertion piece 65 in a manner described above.

Next, the function and advantageous effects of the grasping treatment instrument 1 according to the present embodiment are explained. When treatment is performed using the grasping treatment instrument 1, the end effector 10 is inserted into a body cavity such as an abdominal cavity. Then a treated target such as living tissue is arranged between the pair of grasping pieces 11 and 12, and a space between these grasping pieces 11 and 12 is closed by operating the handle 8. In the end effector 10, the treated target is thus grasped between the grasping pieces 11 and 12. The treated target is then treated by supplying treatment energy such as ultrasonic vibration or high-frequency electric energy to the end effector 10 by operating the operation button 17A or 17B.

In treatment performed by the end effector 10 using treatment energy, friction heat by ultrasonic vibration, heat by high-frequency current, etc. are generated. Thus, the heat generated in treatment increases the temperature of the clamp opposed surface 35 of the clamp member 25 and its vicinity. In the clamp member 25, the heat generated in treatment is conducted toward the clamp back surface 45 and the clamp side surfaces 46A and 46B (toward the back surface side). In the present embodiment, the cover member 30 is attached to the clamp member 25 from the back surface side and covers the clamp member 25 from the back surface side and both sides in the width directions of the second grasping piece 12. In this manner, the clamp member 25 is effectively prevented from coming in contact with living tissue other than a treated target through portions (such as the clamp back surface 45, the clamp side surfaces 46A and 46B, etc.) other than the clamp opposed surface 35. The cover member 30 is made of a material having lower heat conductivity than the clamp member 25. Accordingly, even when the cover member 30 comes in contact with living tissue other than a treated target, heat damage of the living tissue can be effectively prevented.

In the present embodiment, the clamp member 25 is prevented from coming in contact with living tissue other than a treated target through portions (such as the clamp back surface 45, the clamp side surfaces 46A and 46B, etc.) other than the clamp opposed surface 35, as described above. Also, the cover member 30 is made of a material having electrical insulation. In this manner, a high-frequency current is effectively prevented from flowing from portions other than the clamp opposed surface 35 into living tissue other than a treated target. Accordingly, a high-frequency current flows through the clamp opposed surface 35 to a treated target in an appropriate manner, thereby securing the treatment performance of treatment using a high-frequency electric energy.

In the present embodiment, each of the engaging holes 56A and 56B as a cover-side engagement engages with its corresponding engaging convex section (55A or 55B) as a clamp-side engagement by snap fitting. By this engagement, the cover member 30 is attached to the clamp member 25 from the back surface side. Each of the engaging holes 56A and 56B engages with its corresponding engaging convex section (55A or 55B) by snap fitting. By this engagement, the cover member is attached to the clamp member 25 easily and appropriately.

The first engaging convex section 55A is provided in the first clamp side surface 46A facing to one side in the width directions of the second grasping piece 12 in the clamp member 25. The first engaging hole 56A of the first cover side wall 52A of the cover member 30 engages with this first engaging convex section 55A by snap fitting. The second engaging convex section 55B is provided in the second clamp side surface 46B facing to the opposite side of the first clamp side surface 46A in the clamp member 25. The second engaging hole 56B of the second cover side wall 52B of the cover member 30 engages with this second engaging convex section 55B by snap fitting. That is, the clamp member 25 engages with the cover member 30 by snap fitting through each of both side surfaces in the width directions of the second grasping piece 12. In this manner, removal of the cover member 30 from the clamp member 25 is effectively prevented.

The clamp member 25 is swingable around the swing axis Y with respect to the supporting member 21. The cover member 30 swings together with the clamp member 25 with respect to the supporting member 21. The cover member 30 swings together with the clamp member 25. This makes it even harder for the cover member 30 to be removed from the clamp member 25.

In a state where the cover member 30 is attached to the clamp member 25, an elastic force acts on the cover member 30 toward the opposed surface side so that the cover member 30 comes in close contact with the clamp member 25 (the clamp base 41 and the clamp projection 42) without any clearance, on the outer surface of the second grasping piece 12. In this manner, the cover member 30 and the clamp member 25 are effectively prevented from having a dirt material, etc. sandwiched therebetween on the outer surface of the second grasping piece 12. This makes it even harder for the cover member 30 to be removed from the clamp member 25.

In the present embodiment, the insertion piece 65 of the cover member 30 is inserted between the supporting member 21 and the clamp member 25 in the open and close directions of the second grasping piece 12. The regulating projection 63 of the clamp member 25 and the member back wall 31 of the supporting member 21 regulate movement of the insertion piece 65 in a manner wherein the insertion piece 65 is prevented from being removed from the space between the supporting member 21 and the clamp member 25. The insertion piece 65 is prevented from being removed from the space between the supporting member 21 and the clamp member 25. In this manner, removal of the cover member 30 from the clamp member 25 is effectively prevented even in a state where each of the engaging convex sections 55A and 55B disengages from its corresponding engaging hole (56A or 56B) in the part of engagement by snap fitting.

In the present embodiment, furthermore, the clamp member 25 is swingably coupled to the supporting member 21. In this manner, heat transference from the clamp member 25 to the supporting member 21 is not increased. Accordingly, the temperature is not increased in the outer surface of the supporting member 21. Even if the supporting member 21 comes in contact with living tissue other than a treated target, heat damage of the living tissue is thus effectively prevented.

In addition, in the present embodiment, the supporting member 21 is fixed to the handle 8. This increases heat transference from the supporting member 21 to the handle 8, and enlarges heat capacity of the supporting member 21. Therefore, heat damage of living tissue by the supporting member 21 is even more effectively prevented.

(Modifications)

Figure 7:
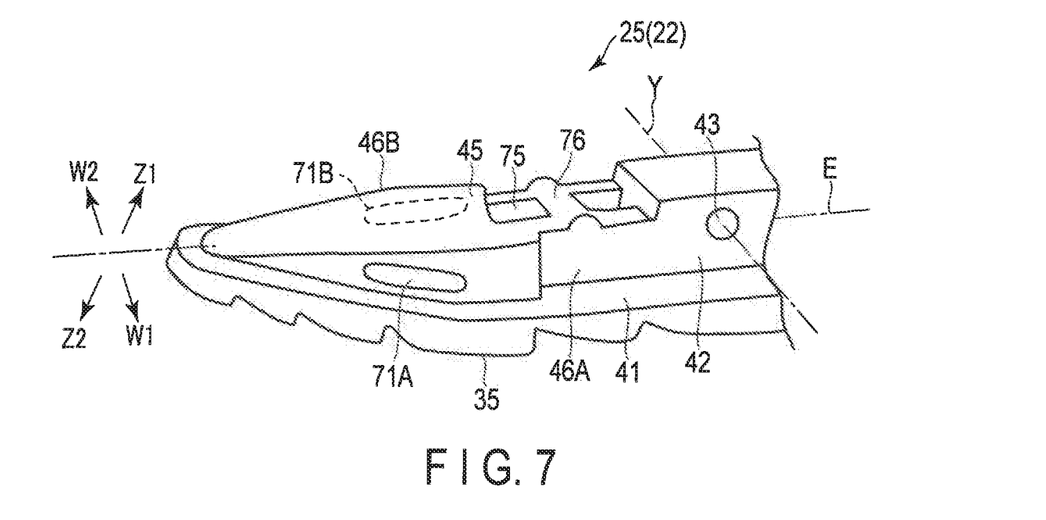
FIG. 7 is a perspective view schematically showing a clamp member according to a first modification.
Figure 8:
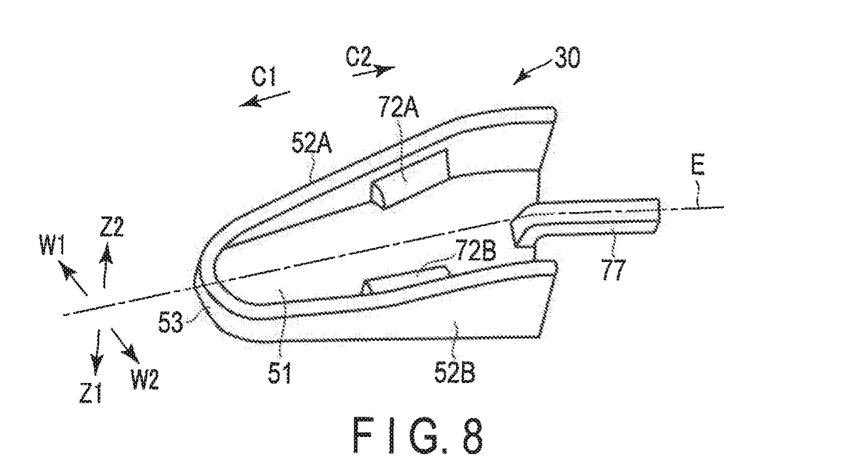
FIG. 8 is a perspective view schematically showing a cover member according to the first modification.
Figure 9:
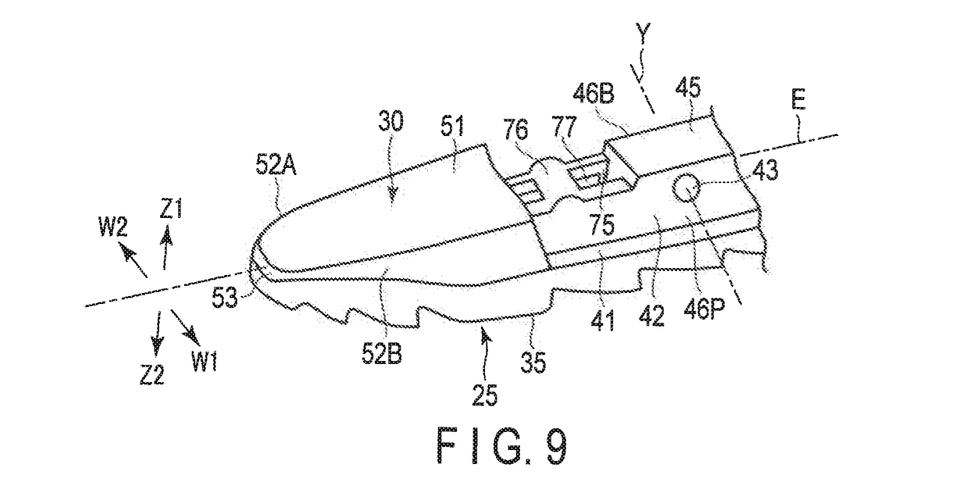
FIG. 9 is a perspective view schematically showing the clamp member and the cover member according to the first modification.

In the first modification shown in FIGS. 7 to 9, the clamp member 25 is not provided with the engaging convex sections 55A and 55B. Instead, the first clamp side surface 46A is provided with a first engaging concave section 71A that is concaved to the inside (the side toward the extending axis E) in the width directions of the second grasping piece 12 (the directions indicated by the arrows W1 and W2 in each of FIGS. 7 to 9). The second clamp side surface 46B is provided with a second engaging concave section 71B that is concaved to the inside (the side toward the extending axis E) in the width directions of the second grasping piece. The engaging concave sections 71A and 71B are provided in the clamp projection 42, and are formed in the distal portion of the clamp member 25. The engaging concave sections 71A and 71B are positioned on the distal side with respect to the swing axis Y and the distal end of the supporting member 21.

In this modification, the cover member 30 is not provided with the engaging holes 56A and 56B. Instead, the first cover side wall 52A is provided with a first engaging convex section 72A that projects to the inside in the width directions of the second grasping piece 12. The second cover side wall 52B is provided with a second engaging convex section 72B that projects to the inside in the width directions of the second grasping piece 12. The engaging convex sections 72A and 72B are positioned on the distal side with respect to the proximal end of the cover back wall 51 and the proximal ends of the cover side walls 52A and 52B.

The first engaging convex section (the first cover-side engaging section) 72A engages with the first engaging concave section (the first clamp-side engaging section) 71A by snap fitting. The second engaging convex section (the second cover-side engaging section) 72B engages with the second engaging concave section (the second clamp-side engaging section) 71B by snap fitting. Each of the engaging convex sections 72A and 72B engages with its corresponding engaging concave section (71A or 71B). By this engagement, the cover member 30 is attached to the clamp member 25 from the back surface side. In this modification as well, the cover member 30 to be attached to the clamp member 25 swings together with the clamp member 25 and the pad member 26 around the swing axis Y with respect to the supporting member 21. Also in this modification, the clamp member 25 is not exposed to the outside in the part of engagement by snap fitting between each of the engaging concave sections 71A and 71B, and its corresponding engaging convex section (72A or 72B).

In this modification, the clamp member 25 is not provided with the locking projection 62 and the regulating projection 63. Instead, a groove 75 is extended along the extending axis E in the clamp back surface 45 of the clamp member 25 (the clamp projection 42). On the clamp back surface 45, the groove 75 is concaved to the opposed surface side (the side indicated by the arrow Z2 in each of FIGS. 7 to 9) of the second grasping piece 12. The groove 75 is formed between the swing axis Y and the engaging concave sections 71A and 71B in the direction along the extending axis E. On the clamp back surface 45 of the clamp member 25, a regulating piece section 76 is extended in the width directions of the second grasping piece 12. The regulating piece section 76 is formed across the full width of the clamp projection 42 in the width directions of the second grasping piece 12. The regulating piece section 76 is positioned within a range in which the groove 75 is extended in the direction along the extending axis E. The opening of the groove 75 is partially blocked by the regulating piece section 76.

The cover member 30 in this modification includes an insertion piece 77 that projects to the proximal side with respect to the proximal end of the cover back wall 51 and the proximal ends of the cover side walls 52A and 52B. The insertion piece 77 forms the proximal end of the cover member 30. In this modification as well, the insertion piece 77 of the cover member 30 is inserted from the distal side, between the supporting member 21 and the clamp member 25 in the open and close directions of the second grasping piece 12. In this modification, the insertion piece 77 is inserted into the groove 75 of the clamp member 25. In a state where the insertion piece 77 is inserted into the groove 75, the insertion piece 77 is positioned on the distal side with respect to the swing axis Y.

In this modification, the regulating piece section 76 of the clamp member 25 regulates removal of the insertion piece 77 from the groove 75. Accordingly, the insertion piece 77 is not removed from the space between the supporting member 21 and the clamp member 25 no matter where the clamp member 25 is positioned with respect to the supporting member 21. In this modification, the regulating piece section 76 of the clamp member 25 regulates movement of the insertion piece 77 in a manner wherein the insertion piece 77 is prevented from being removed from the space between the supporting member 21 and the clamp member 25. The regulating piece section 76 forms a regulating section that regulates movement of the insertion piece 77 in a manner described above.

This modification produces the similar function and advantageous effects to those of the first embodiment. Furthermore, in this modification, the clamp member 25 is not exposed to the outside in the part of engagement by snap fitting between each of the engaging concave sections 71A and 71B, and its corresponding engaging convex section (72A or 72B). Thus, the clamp member 25 is even more effectively prevented from coming in contact with living tissue other than a treated target through portions (such as the clamp back surface 45, the clamp side surfaces 46A and 46B, etc.) other than the clamp opposed surface 35.

Figure 10:
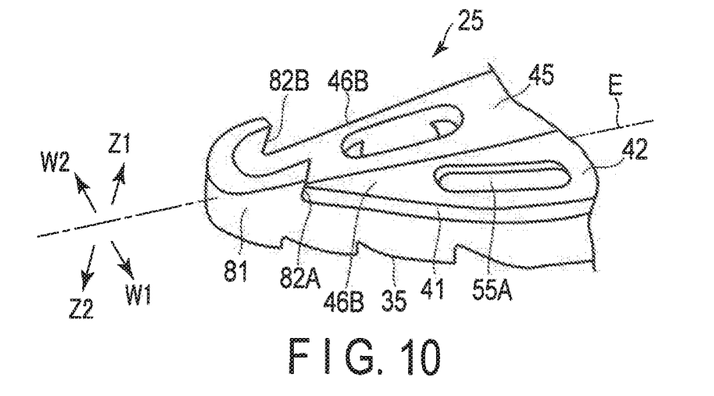
FIG. 10 is a perspective view schematically showing a clamp member according to a second modification.
Figure 11:
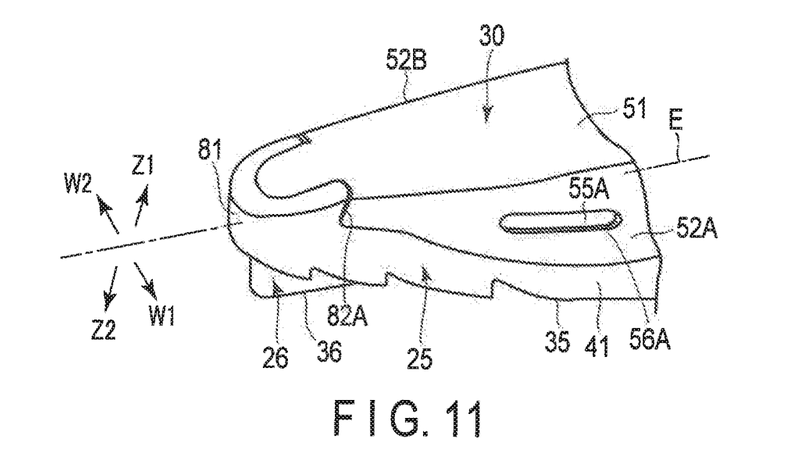
FIG. 11 is a perspective view schematically showing a second grasping piece according to the second modification.

In the second modification shown in FIGS. 10 and 11, the distal portion of the clamp member 25 is provided with a distal projection 81. The distal projection 81 projects to the back surface side (the side indicated by the arrow Z1 in each of FIGS. 10 and 11) with respect to the clamp base 41, and also projects to the back surface side (the side to which the second grasping piece 12 is moved in its opening action) with respect to the clamp projection 42. The distal projection 81 is continuous to the distal side of the clamp projection 42 and forms a part of the distal surface of the second grasping piece 12 (a part of the distal surface of the clamp member 25). The distal projection 81 is formed across the entire width of the second grasping piece 12 in the width directions (the directions indicated by the arrows W1 and W2 in each of FIGS. 10 and 11) and forms a part of the back surface of the second grasping piece 12.

In this modification, the cover member 30 is not provided with the cover distal wall 53. The cover member 30 is, however, provided with the cover back wall 51 and the cover side walls 52A and 52B, as in the first embodiment.

The distal projection 81 is provided with a first abutting section 82A on which the distal end of the first cover side wall 52A abuts. The first abutting section 82A presses the first cover side wall 52A toward the opposed surface side (the side indicated by the arrow Z1 in each of FIGS. 10 and 11). The distal projection 81 is provided with a second abutting section 82B on which the distal end of the second cover side wall 52B abuts. The second abutting section 82B presses the second cover side wall 52B toward the opposed surface side (the side to which the second grasping piece 12 is moved in its closing action). Each of the cover side walls 52A and 52B is pressed by its corresponding abutting section (82A or 82B). This pressing makes it even harder for the cover member 30 to be removed from the clamp member 25.

Figure 12:
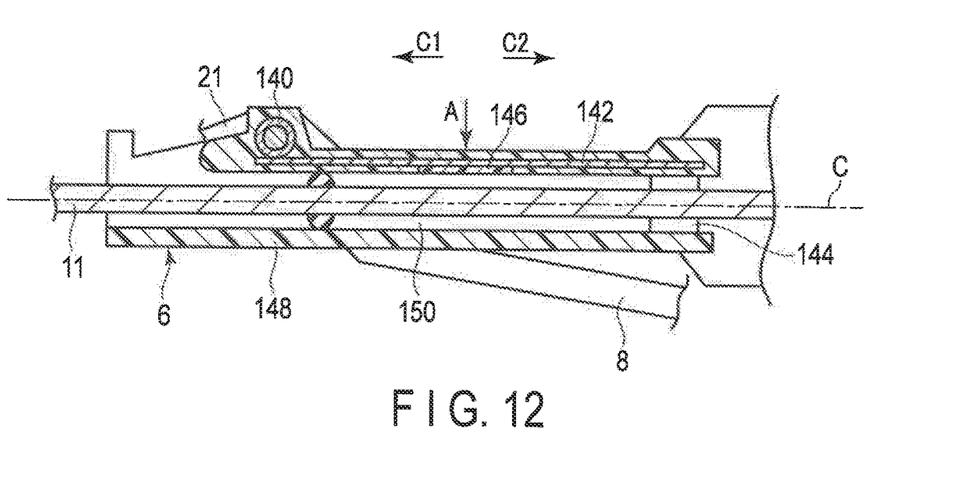
FIG. 12 is a cross-sectional view, taken in a cross section perpendicular to a longitudinal axis, showing a sheath according to a reference example.

FIG. 12 shows a cross section along the longitudinal axis C of the sheath 6, as a reference example. The sheath 6 includes a bearing 140, a flat plate 142, and a ring 144, each made from a conductive material such as metal. In the sheath 6, the bearing 140, the flat plate 142, and the ring 144 are welded, and integrally form a conductive unit (a metal unit). The sheath 6 is formed by insert-molding a first resin material 146 and a second resin material 148 into this conductive unit. The second resin material 148 has electrical insulation, and one example is PEEK. The first resin material 146 has electrical insulation and a higher melting point than the second resin material 148. One example of the first resin material 146 is polycarbonate. The first resin material 146 is fixed to the metal unit (the flat plate 142) and is positioned closer to the longitudinal axis C than the flat plate 142. High-frequency electric energy, to be supplied through wirings (not shown) inside the cable 16 and a conductive section (not shown) of the transducer unit 15, is supplied to the supporting member 21 of the second grasping piece 12 through the ring 144, the flat plate 142, and the bearing 140 in order. An inner cavity 150 is formed inside the sheath 6.

To form the sheath 6, the first resin material 146 is fixed on the side close to the longitudinal axis C of the flat plate 142, and in this state, they are installed in a die. The second resin material 148 is then injected from an injection port A shown in FIG. 12, which communicates with an injection port of the die. At this time, the second resin material 148 is injected from the side (the side opposite to the side to which the first resin material 146 is fixed) that is substantially perpendicular to the longitudinal axis C and is distant from the longitudinal axis C. Accordingly, in a state where the second resin material 148 is injected, the flat plate 142 is deformed, even when deformed by resin pressure, toward the side close to the longitudinal axis C (the inner cavity 150 side). In the resultant sheath 6, therefore, the flat plate 142 is not exposed at the exterior (the surface on the side distant from the longitudinal axis C). This prevents high-frequency current (high-frequency electric energy) from flowing through the exterior of the sheath 6. The second resin material 148 is injected in a state where the first resin material 146 is fixed on the side close to the longitudinal axis C of the flat plate 142. This prevents the flat plate 142 from being positioned on the side (the inner cavity 150 side) close to the longitudinal axis C beyond the first resin material 146, even when the flat plate 142 is deformed by resin pressure of the second resin material to be injected. In the resultant sheath 6, therefore, the flat plate 142 is not exposed at the surface on the inner cavity 150 side (the surface on the side close to the longitudinal axis C). This prevents high-frequency current (high-frequency electric energy) from flowing through the surface of the sheath 6, on the inner cavity 150 side.

Figure 13:
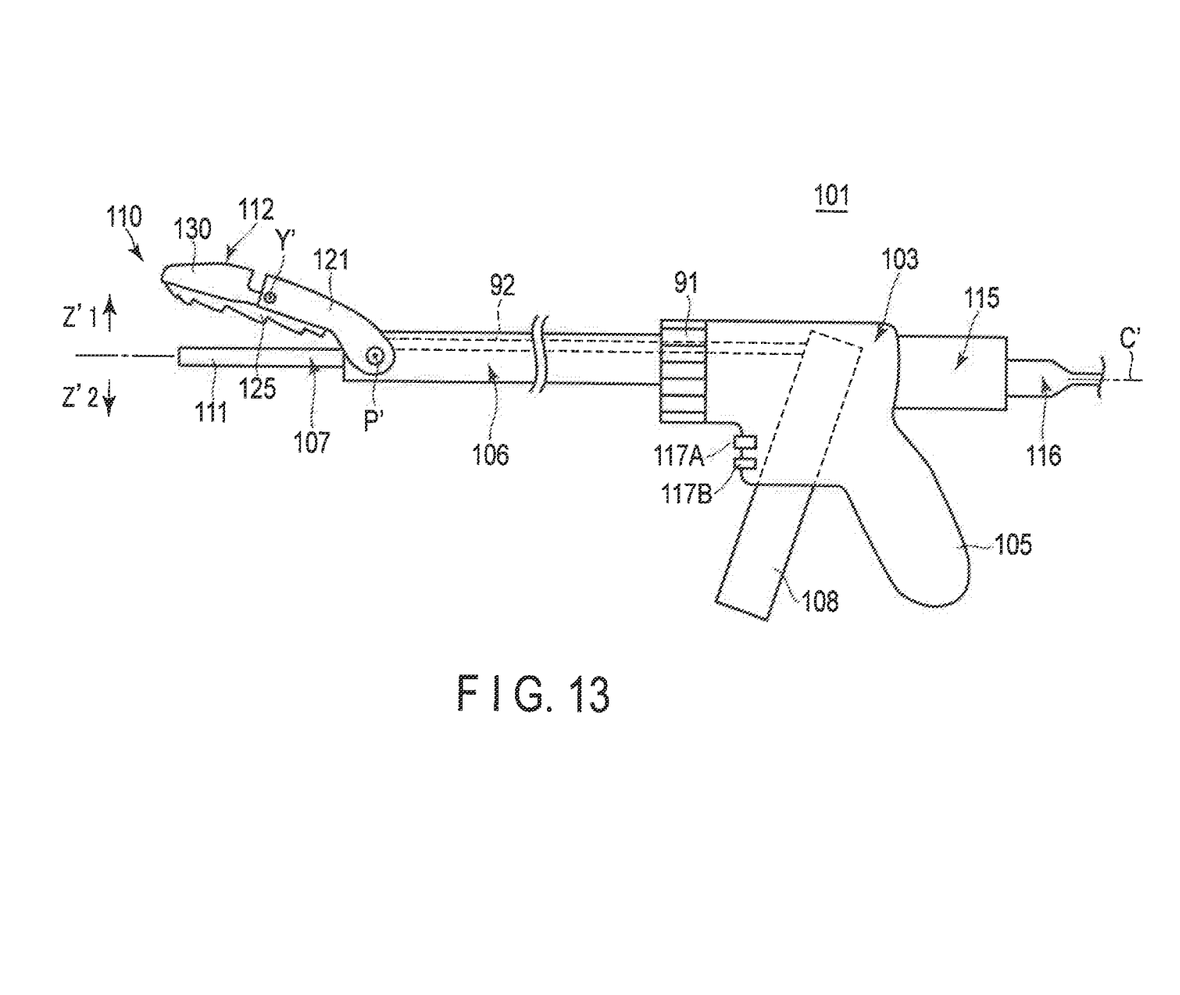
FIG. 13 is a schematic diagram showing a grasping treatment instrument according to a third modification.

In a grasping treatment instrument 101 shown in FIG. 13 as the third modification, a handle 108 is not fixed to a supporting member 121 of a second grasping piece 112. Also in this modification, similar to the embodiments and the like described above, the grasping treatment instrument 101 includes a housing 103, a sheath 106, a rod 107, an end effector 110, a transducer unit 115, and a cable 116. In the housing 103, a grip 105 is formed and operation buttons 117A and 117B are attached. In the rod 107, furthermore, a part projecting from the distal end of the sheath 106 to the distal side forms a first grasping piece 111 of the end effector 110.

In this modification, however, the handle 108 is rotatably attached to the housing 103 and is positioned on the same side as the grip 105 with the longitudinal axis C as a center. The handle 108 moves substantially parallel to the longitudinal axis C by rotating with respect to the housing 103. In this manner, the handle 108 is opened or closed with respect to the grip 105. In this modification, a rotation knob 91 is attached to the distal side of the housing 103. The sheath 106 and the end effector 110 rotate together with the rotation knob 91 around the longitudinal axis C by causing the rotation knob 91 to rotate around the longitudinal axis C with respect to the housing 103.

Furthermore, in this modification, a movable body 92 is extended along the longitudinal axis C from the inside of the housing 103 through the inside of the sheath 106. Inside the housing 103, the handle 108 is coupled to the movable body 92. The distal end of the movable body 92 is connected to the second grasping piece 112. The movable body 92 is moved along the longitudinal axis C with respect to the sheath 106 by opening or closing the handle 108 with respect to the grip 105. In this manner, the second grasping piece 112 is opened or closed with respect to the first grasping piece 111.

The second grasping piece 112 has the same configuration as in any one of the embodiments and the like described above. The supporting member 121 is attached to the distal portion of the sheath 106, in a manner to be rotatable around a rotation axis P'. The clamp member 125 is attached to the supporting member 121 in a manner to be swingable with a swing axis Y' as a center. The cover member 130 is attached to the distal portion of the clamp member 125, from the back surface side (the side indicated by the arrow Z'1 in FIG. 13).

In this modification, the second grasping piece 112 has the same configuration as in any of the embodiments and the like described above. Thus, this modification also produces the similar functions and advantageous effects to those of the embodiments and the like described above.

In the embodiments, etc. described above, ultrasonic vibration and high-frequency electric energy are supplied to the end effector (10; 110), as treatment energy for use in treatment. Treatment energy to be supplied to the end effector (10; 110), however, is not limited to this.

In the embodiments and the like described above, the grasping treatment instrument (1; 101) includes the grasping piece (11; 111), the supporting member (21; 121) that is opened and closed with respect to the grasping piece (11; 111), and the clamp member (25; 125) that is pivotally supported by the supporting member (21; 121). The clamp member (25; 125) is provided between the supporting member (21; 121) and the grasping piece (11; 111) in the open and close directions (Z1, Z2; Z'1, Z'2) of the supporting member (21; 121). The clamp member (25; 125) includes the opposed surface (35) opposed to the grasping piece (11; 111) and the back surface (45) facing to the opposite side of the opposed surface (35). The grasping treatment instrument (1; 101) includes the cover member (30; 130) made of a material having lower thermal conductivity than the clamp member (25; 125). The cover member (30; 130) is attached to the distal portion of the clamp member (25; 125), from the back surface side, and covers the clamp member (25; 125) from the back surface side, in a part on the distal side with respect to the position where the clamp member (25; 125) is pivotally supported.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment instrument comprising:
   a first grasping piece; and
   a second grasping piece that is configured to open and close with respect to the first grasping piece to grasp a treated target, the second grasping piece including:
     a supporting member which is configured to open and close with respect to the first grasping piece;
     a clamp member which is pivotally supported by the supporting member, and which is provided between the supporting member and the first grasping piece in open and close directions of the supporting member, the clamp member including an opposed surface which is opposed to the first grasping piece, and a back surface which faces to an opposite side of the opposed surface; and
   a cover member which is made of a material having lower thermal conductivity than the clamp member, and which is attached to the clamp member from a back surface side, the cover member covering the clamp member from the back surface side in a part on a distal side with respect to a position where the clamp member is pivotally supported,
   wherein a proximal end of the cover member is positioned on the distal side with respect to the position where the clamp member is pivotally supported by the supporting member.

2. The grasping treatment instrument according to claim 1, wherein the cover member is configured to swing together with the clamp member with respect to the supporting member.

3. The grasping treatment instrument according to claim 1, the cover member includes an insertion piece which is inserted between the supporting member and the clamp member in the open and close directions of the supporting member.

4. The grasping treatment instrument according to claim 3, wherein at least one of the supporting member and the clamp member includes a regulating section which is configured to regulate movement of the insertion piece in a manner wherein the insertion piece is prevented from being removed from a space between the supporting member and the clamp member.

5. The grasping treatment instrument according to claim 1, further comprising a handle which is fixed to the supporting member, and which is configured to rotate together with the supporting member with respect to the first grasping piece around a rotation axis intersecting with the open and close directions of the supporting member in a state where the supporting member is opened or closed with respect to the first grasping piece.

6. The grasping treatment instrument according to claim 1, wherein
the clamp member includes a clamp-side engaging section, and
the cover member includes a cover-side engaging section which is configured to attach the cover member to the clamp member from the back surface side by engaging with the clamp-side engaging section by snap fitting.

7. The grasping treatment instrument according to claim 6, wherein
the clamp member includes a first side surface and a second side surface, the first side surface facing to one side in width directions of the clamp member, the width directions intersecting with extension directions of the clamp member and intersecting with the open and close directions of the supporting member, the second side surface facing to an opposite side of the first side surface,
the cover member includes a first side wall and a second side wall, the first side wall covering the first side surface from the one side of the width directions of the clamp member, the second side wall covering the second side surface from the opposite side of the first side wall,
the clamp-side engaging section includes a first clamp-side engaging section and a second clamp-side engaging section, the first clamp-side engaging section being provided on the first side surface, the second clamp-side engaging section being provided on the second side surface, and
the cover-side engaging section includes a first cover-side engaging section and a second cover-side engaging section, the first cover-side engaging section being provided in the first side wall and engaging with the first clamp-side engaging section by snap fitting, the second cover-side engaging section being provided in the second side wall and engaging with the second clamp-side engaging section by snap fitting.

8. The grasping treatment instrument according to claim 4, wherein
the regulating section includes a projection, and
the insertion piece is formed in a ring shape having a hole through which the projection is inserted.

9. The grasping treatment instrument according to claim 1, wherein the proximal end of the cover member is positioned between a distal end of the supporting member and the position where the clamp member is pivotally supported by the supporting member.

10. The grasping treatment instrument according to claim 1, wherein the second grasping piece further comprises a pad member and the pad member extends in a direction along an extending axis from a proximal portion to a distal portion of the clamp member, and the pad member includes an abutting surface that is opposed to the first grasping piece and is configured to abut on the first grasping piece.

11. The grasping treatment instrument according to claim 10, wherein the pad member is made of a material having electrical insulation.

12. The grasping treatment instrument according to claim 1, further comprising a sheath which is extended along the longitudinal axis from a proximal side to the distal side,
wherein the supporting member is rotatably attached to a distal portion of the sheath so that the second grasping piece is configured to open and close with respect to the first grasping piece to grasp the treated target.

* * * * *